(12) United States Patent
Riedel

(10) Patent No.: US 6,323,495 B1
(45) Date of Patent: Nov. 27, 2001

(54) METHOD AND APPARATUS FOR THE DETERMINATION OF PHASE DELAY IN A LIFETIME FLUOROMETER WITHOUT THE USE OF LIFETIME STANDARDS

(75) Inventor: Richard A. Riedel, Carmel, IN (US)

(73) Assignee: UMM Electronics, Inc., Indianapolis, IN (US)

( * ) Notice: Subject to any disclaimer, the term of this patent is extended or adjusted under 35 U.S.C. 154(b) by 0 days.

(21) Appl. No.: 09/506,819

(22) Filed: Feb. 18, 2000

Related U.S. Application Data

(60) Provisional application No. 60/155,932, filed on Sep. 24, 1999.

(51) Int. Cl.[7] .................................................. G01N 21/64
(52) U.S. Cl. .................................. 250/458.1; 250/461.2; 250/459.1
(58) Field of Search ............................. 250/458.1, 461.2, 250/459.1

(56) References Cited

U.S. PATENT DOCUMENTS

| | | |
|---|---|---|
| 4,058,732 | 11/1977 | Wieder . |
| 4,105,333 | 8/1978 | Kaule et al. . |
| 4,198,567 | 4/1980 | Eneroth et al. . |
| 4,507,562 | 3/1985 | Gasiot et al. . |
| 4,549,807 | 10/1985 | Hoffmaster . |
| 4,778,593 | 10/1988 | Yamashita et al. . |
| 4,910,467 | 3/1990 | Leitch . |
| 5,043,585 | 8/1991 | Fehrenbach et al. . |
| 5,315,122 | 5/1994 | Pinsky et al. . |
| 5,317,162 | 5/1994 | Pinsky et al. . |
| 5,324,635 | 6/1994 | Kawase et al. . |
| 5,334,841 | 8/1994 | Graessle et al. . |
| 5,485,530 | 1/1996 | Lakowicz et al. . |

*Primary Examiner*—Constantine Hannaher
*Assistant Examiner*—Andrew Israel
(74) *Attorney, Agent, or Firm*—Woodard, Emhardt, Naughton, Moriarty & McNett

(57) ABSTRACT

A method for measuring the fluorescent lifetime of an unknown fluorescent sample, such as a biological liquid, without the requirement of manual intervention or a separate reference standard. An energetic light beam having its low energy component filtered out is shined on the sample. An optical detector is positioned such that the intensity of the components of the light beam reflected from the sample reaching the detector is substantially minimized but light remitted and/or fluoresced by the sample does reach the detector with non-trivial intensity. Errors arising from the electronic components of the system, such as RFI and D.C. offset errors, are isolated and minimized by positioning an opaque filter between the sample and the detector and measuring the resulting signal. The resulting baseline measurement data is stored for later error subtraction. A low-pass filter is selectively placed between the sample and the detector to isolate the high-energy remitted light component coming from the sample and having the same phase as the original energetic beam used to stimulate fluorescence, and a high-pass filter selectively is placed between the sample and the detector to isolate the lower-energy fluoresced light component coming from the sample. The phases of each component are then measured and compared to determine the phase shift of the light fluoresced by the sample, and the phase shift data is used to calculate the fluorescent lifetime of the sample according to tan $\phi = \omega\tau$.

20 Claims, 5 Drawing Sheets

METHOD AND APPARATUS FOR THE DETERMINATION OF PHASE DELAY IN A LIFETIME FLUOROMETER WITHOUT THE USE OF LIFETIME STANDARDS

CROSS-REFERENCE TO RELATED APPLICATIONS

This application claims priority to U.S. Provisional Application Serial No. 60/155,932 filed Sep. 24, 1999.

TECHNICAL FIELD OF THE INVENTION

The present invention relates generally to fluorometry and, more particularly, to a novel method and apparatus for measuring fluorescent lifetime by determining the phase difference between a reference signal and a fluorescent sample signal without the use of a lifetime standard.

BACKGROUND OF THE INVENTION

Fluorometry is an important quick and nondestructive analytical chemistry technique. Fluorometry is used to acquire both qualitative and quantitative data, and is of great interest for use in clinical chemistry and medical diagnostics as a means for measuring unknowns such as the pH and partial pressure of blood gasses and blood analytes.

In general, fluorometric analysis involves shining an energetic light onto a sample and stimulating the immediate re-emission or fluorescence of light of a particular frequency from the sample. The frequency of the light so fluoresced is characteristic of the particular sample component fluorescing. The frequency of the light shined onto the sample is usually chosen to be slightly higher than that of the frequency of the light characteristically fluoresced by the sample component desired to be measured. In other words, the fluoresced light has an energy less than or equal to that of the light source, since conservation of energy and the quantum nature of light dictate that the fluoresced photons cannot be more energetic than the excitation photons absorbed to produce the fluoresced photons.

The intensity of the fluoresced light is proportional to the quantity of the fluoresced sample. The fluorescence from the excited sample also has a finite and measurable lifetime. The fluorescent lifetime of a given material can be changed by the presence of an analyte such as oxygen and Ru(dpp)$_3$ and can be the basis of quantitative analysis. The motivation to use fluorescent lifetime measurements instead of intensity-based fluorescent measurements arises from the relative immunity of fluorescent lifetime measurements from many of the potential sources of error to which intensity measurements are prone. Examples of sources of error afflicting fluorescent intensity measurements include variations in the intensity of the light source or quantum efficiency of the detector, opacity or scattering characteristics of the sample medium, and geometrical differences between the source and the detector. By measuring the fluorescent lifetime instead of the fluorescent intensity, especially in biological samples, most or all of these sources of measurement error are minimized or eliminated.

There are two techniques commonly used to measure fluorescent lifetime: the pulse method and the harmonic modulation method. The pulse method involves measuring the lifetime of the fluoresced signal by fluorescing a sample with a pulsed source signal and measuring the pulse response of the fluorescent signal. The lifetime of the corresponding fluorescent pulse is measured in the time domain and an estimate of the lifetime is obtained by fitting a theoretical curve to the data.

The second technique for measuring fluorescent lifetime involves measuring the lifetime of the fluorescence in the frequency domain as a phase shift of the detected signal relative to the source signal. The relationship between the phase shift $\phi$ and the lifetime $\tau$ for a single lifetime fluorescent indicator expressed by:

$$\tan \phi = \omega \tau,$$

where $\omega$ is the angular frequency of excitation of a known harmonic. By measuring $\phi$, the fluorescent lifetime $\tau$ can be calculated.

While a number of methods exist which allow the measurement of the phase of a fluoresced signal relative to a reference signal, all of the presently known methods require that the measured phase delay of the fluoresced signal be referenced to the measured phase delay of a fluorescent standard having a known lifetime, for example Rodamine B. This is necessary because all measurement systems have inherent phase delays arising from the measurement electronics. Without the reference standard, the phase measurement would incorporate the phase delay contribution from the electronics in the measurement of an unknown sample's phase delay, giving rise to potentially nontrivial errors. In addition to the referencing of a measured phase delay to a reference standard, some measurement systems, especially those using phase sensitive detection where the sample signal $\Sigma A_n \sin(n\omega\tau + \phi_n)$ is multiplied by a reference signal B $\sin(\omega\tau)$, require the subtraction of "artifacts" due to RF coupling or DC offsets from the measured signal. This typically requires the removal of the sample to ensure correct subtraction of these terms. Because the present methods require user intervention and a reference standard, the need arises for a method of measuring fluorescent lifetime that eliminates both user intervention and the requirement of a separate fluorescent standard. The present invention addresses this need.

SUMMARY OF THE INVENTION

One form of the present invention relates to a method for measuring fluorescent lifetime without the requirement of manual intervention or a separate reference standard, including the steps of shining a filtered energetic beam of light onto a fluorescent sample, selectively filtering the light leaving the fluorescent sample to isolate the remitted and fluoresced components, measuring the selectively filtered light leaving the fluorescent sample, and calculating the fluorescent lifetime of the sample.

Another form of the present invention relates to an apparatus for automatically performing fluorescent lifetime measurements of unknown samples without a reference standard. The apparatus includes a light source for shining a beam of light through a low-pass filter onto an optical sample. The filter allows only the high-energy portion of the source beam to shine onto the sample. A photodetector is positioned to receive remitted and fluoresced light from the sample, and a filter wheel adapted to selectively dispose one of a plurality of emission filters (high-pass, low-pass and opaque) is positioned between the sample and the photodetector to alternately block portions of the light shining from the sample according to their energies. A microprocessor is operationally connected to the light source, the photodetector, and the filter wheel for controlling the light source and filter wheel and receiving and processing data from the photodetector. The microprocessor may calculate a reference phase from the photodetector signal received while the low-pass emission filter is between the sample and the photodetector and may also calculate the lifetime of the fluoresced signal by comparing the phase of the photodetector signal received while the high-pass filter is in place relative to the calculated reference phase and calculating the phase shift between the two.

One object of the present invention is to provide an improved method and apparatus for conducting lifetime fluorescent measurements. Related objects and advantages of the present invention will be apparent from the following description

DETAILED DESCRIPTION OF THE PREFERRED EMBODIMENT

Figure 1:
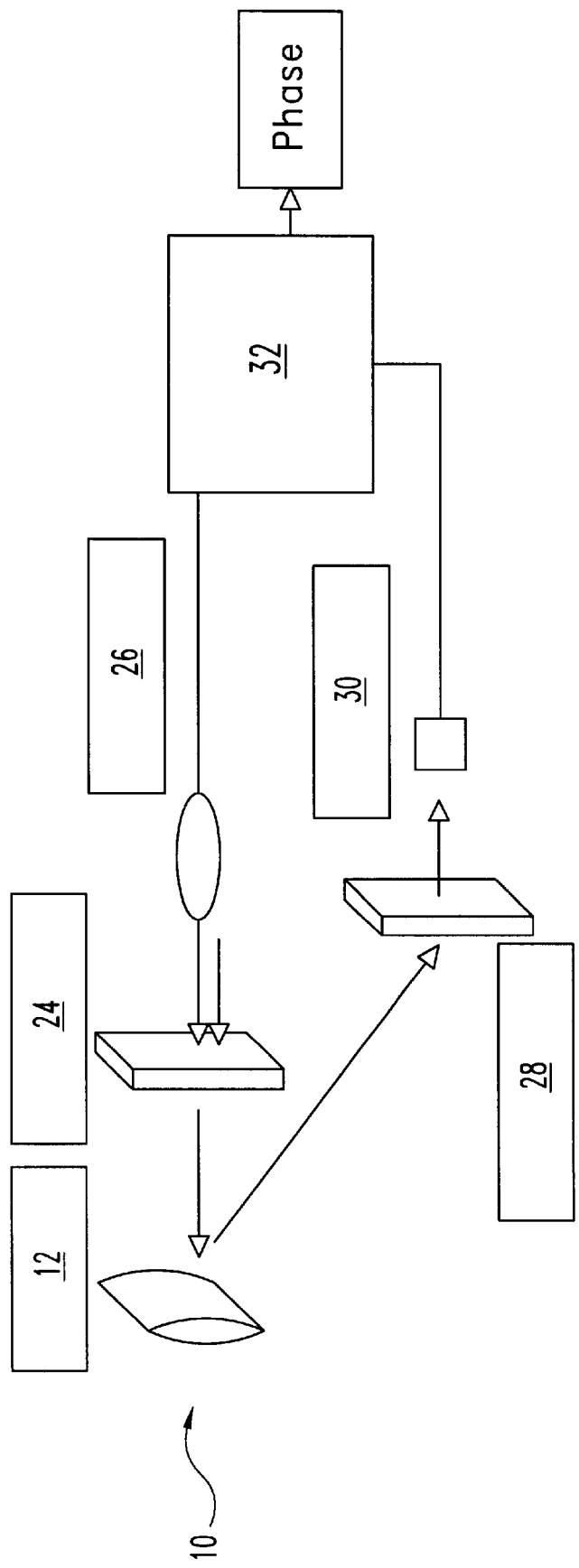
FIG. 1 is a schematic illustration of a first embodiment of the present invention.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Figure 2:
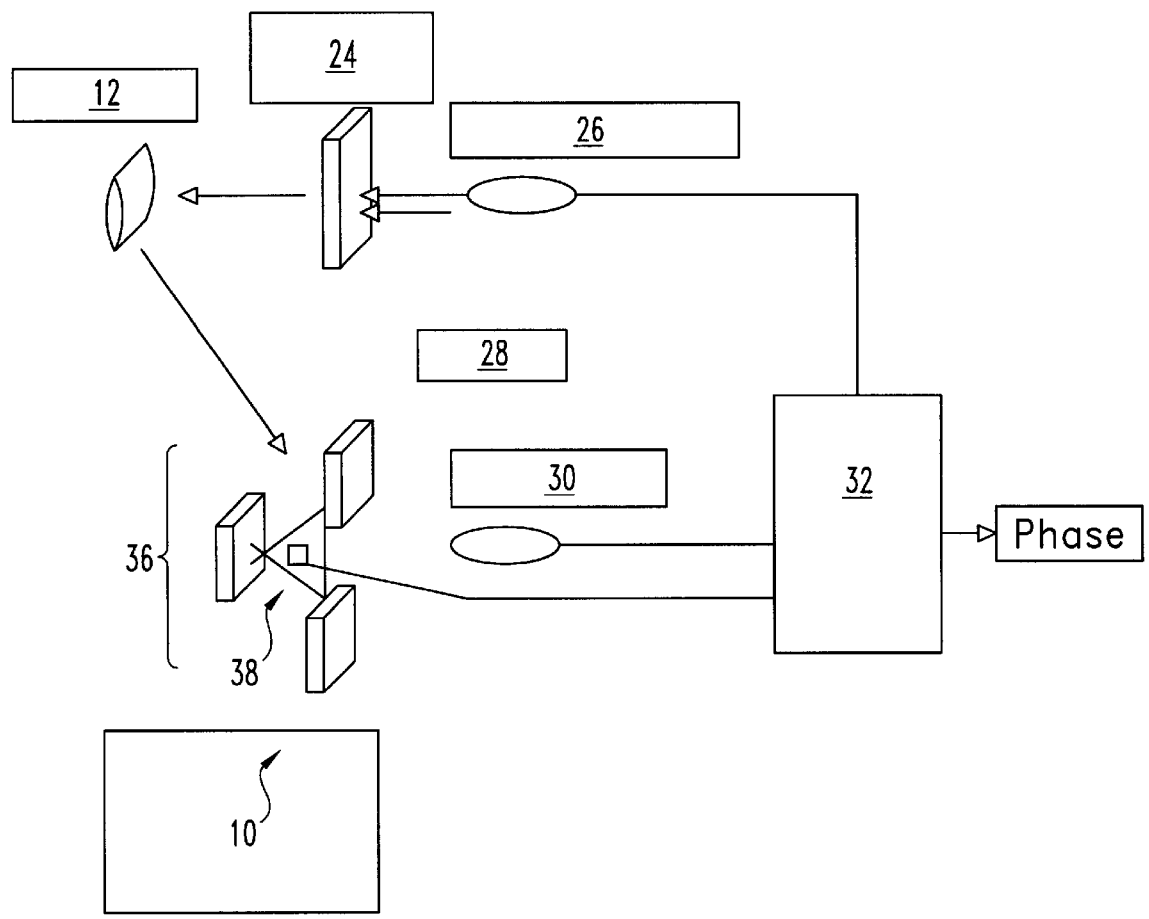
FIG. 2 is a schematic illustration of a second embodiment of the present invention having a motorized emission filter wheel.

The present invention relates to a method and apparatus for measuring fluorescent lifetime without the requirement of manual intervention or the use of a separate reference standard. FIGS. 1 and 2 illustrate one form of the present invention, an apparatus for measuring fluorescent lifetime 10 by determining the phase difference between a remitted reference signal and a fluoresced sample signal without the use of a lifetime fluorescence standard. These various measurements may be made on a single stationary sample 12 by passing an energetic signal beam of light 14 through a variable filter system 16 including opaque, low-pass and high-pass emission filters 28. Variable filter system 16 also includes a source filter 24 positioned between a light source 26 (preferably an LED) and sample 12. Emission filter 28 is positioned between the sample 12 and an optical detector 30. An electronic controller 32 is operationally coupled to both light source 26 and optical detector 30 and is used to control the output signal of light source 26 as well as to analyze the input signal received from optical detector 30.

Source filter 24 is usually chosen to be a low-pass filter and is used to eliminate lower-energy (long wavelength) light components from light beam 14 as generated by light source 26 that could be misinterpreted by optical detector 30 as a fluorescent signal. Emission filter 28 is usually chosen to be a high-pass filter and is used to eliminate the higher-energy, non-fluorescent light wavelengths that pass through source filter 24 and are either remitted or reflected towards optical detector 30, allowing only light wavelengths fluoresced from sample 12 to reach optical detector 30. It is the phase delay or phase shift $\phi$ of the filtered, fluoresced signal relative to the phase of the remitted signal that is of interest. The elimination of the need for a reference standard in making a measurement of the phase shift $\phi$ of the filtered signal is accomplished by alternately using a low-pass emission filter 28 and a high-pass emission filter 28 to selectively filter the light shining from sample 12 onto optical detector 30. With a low-pass emission filter 28 in place between sample 12 and optical detector 30, detector 30 receives only remitted light from sample 12 instead of fluoresced light. Remitted light has no phase delay relative to source beam 14 as emitted from light source 26, and therefore can be used as a phase reference having a lifetime of 0.0 seconds.

RF coupling and DC offset contributions are isolated and quantified by using an opaque emission filter 28. The opaque emission filter 28 blocks all signals from the sample 12, leaving only the contribution arising from the phase delay inherently arising from the electronic components of fluorescent lifetime measurement apparatus 10. The phase delay $\phi^*$ contribution inherent from the hardware is calculated and stored in electronic controller 32 for later error correction by subtraction from the measured phase delays $\phi$ as described above.

In the preferred embodiment illustrated in FIG. 2, the emission filters 28 are part of a system of interchangeable filters positionable to alternately actuate measurements of the baseline phase delay and/or offset contributions from the electronic instrumentation, of the phase of the remitted component of the light shining from sample 12, and of the phase of the fluorescent component of the light shining from sample 12. More preferably, the emission filters 28 are coupled to electronic controller 32 and are adapted to be changed automatically. For example, the emission filters 28 may be mounted to a motorized filter wheel 36 and rotated into and out of place between sample 12 and detector 30 upon actuation of a motor 38 by electronic controller 32.

Generally, the optical values of the low-pass and high-pass emission filter 28 components are chosen relative to the optical character of the unknown fluorescent material desired to be measured. For example, if sample 12 fluoresces at about 500 nm, a 500-nm low-pass emission filter 28 (only passing relatively high energy wavelengths shorter than about 500 nm) is used to obtain the higher-energy remission signal for the determination of the phase of source beam 14. A 550-nm high-pass emission filter 28 (only passing relatively low energy wavelengths longer than about 550 nm) is used to isolate the fluoresced signal for the phase measurement of the fluoresced sample 12. An opaque emission filter 28 that blocks all light is used to isolate the phase error contribution from the electronics inherent in fluorescent lifetime measurement apparatus 10.

Figure 3:
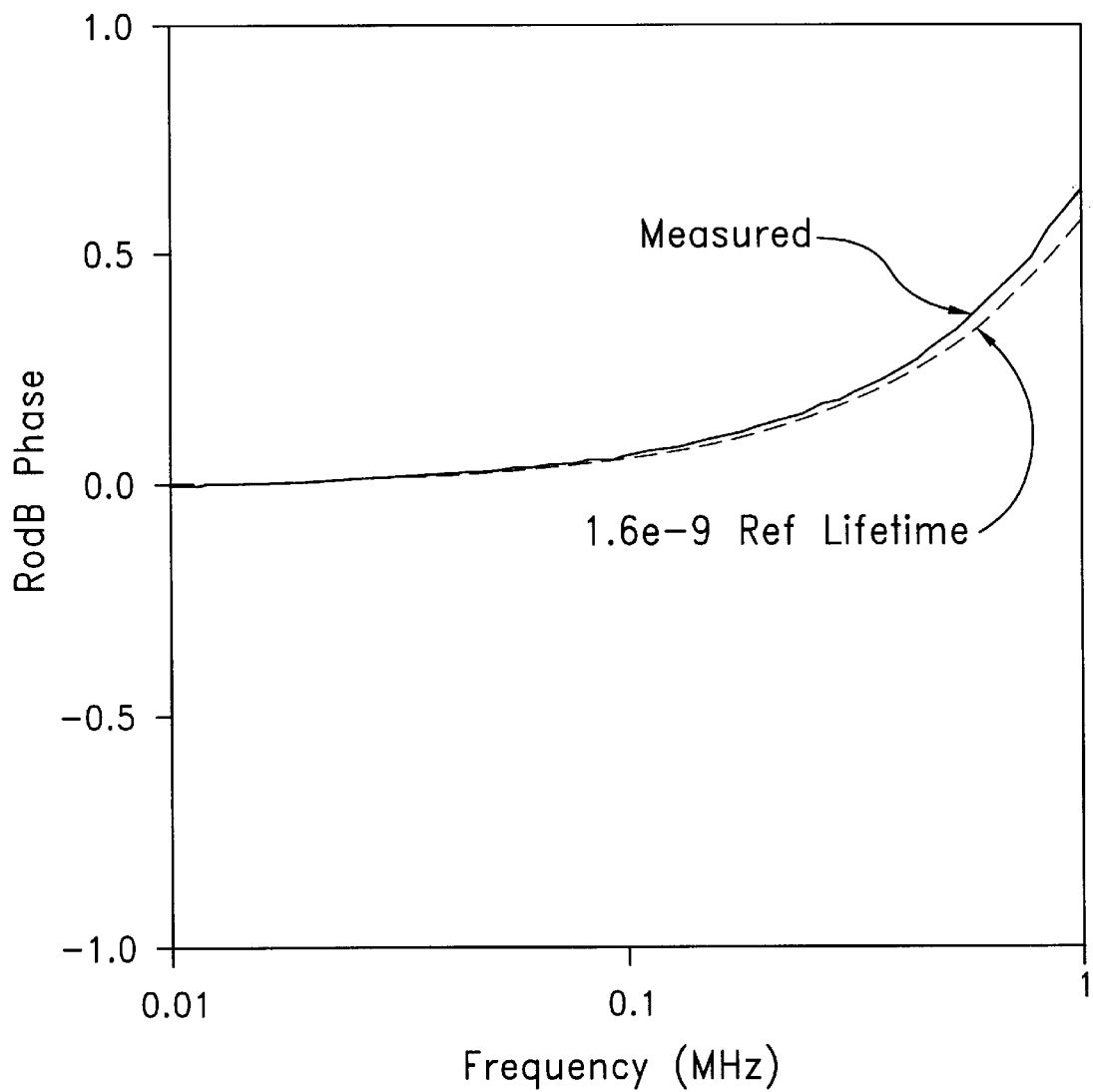
FIG. 3 is a data chart illustrating the relationship between signal phase and signal frequency for a measured sample.

FIG. 3 graphically illustrates the results of a phase measurement of a Rodamine B sample by one embodiment of the present invention. A 500-nm lowpass filter was used as source filter 24. A 500-nm low-pass emission filter 28 was provided to obtain remitted light from sample 12 as a phase reference. An opaque emission filter 28 was then provided to measure the electrical offset and coupling contributions from the electronics. Finally, a 550-nm high-pass emission filter 28 was used to measure the fluoresced signal from fluoresced sample 12.

The solid line represents the phase of the Rodamine B sample measured by the present invention as a function of frequency, while the dashed line represents the well-known theoretical delay of a 1.6 nanosecond lifetime of a Rodamine B fluorescent signal. There is good agreement between the measured value and the accepted theoretical value.

Figure 4:
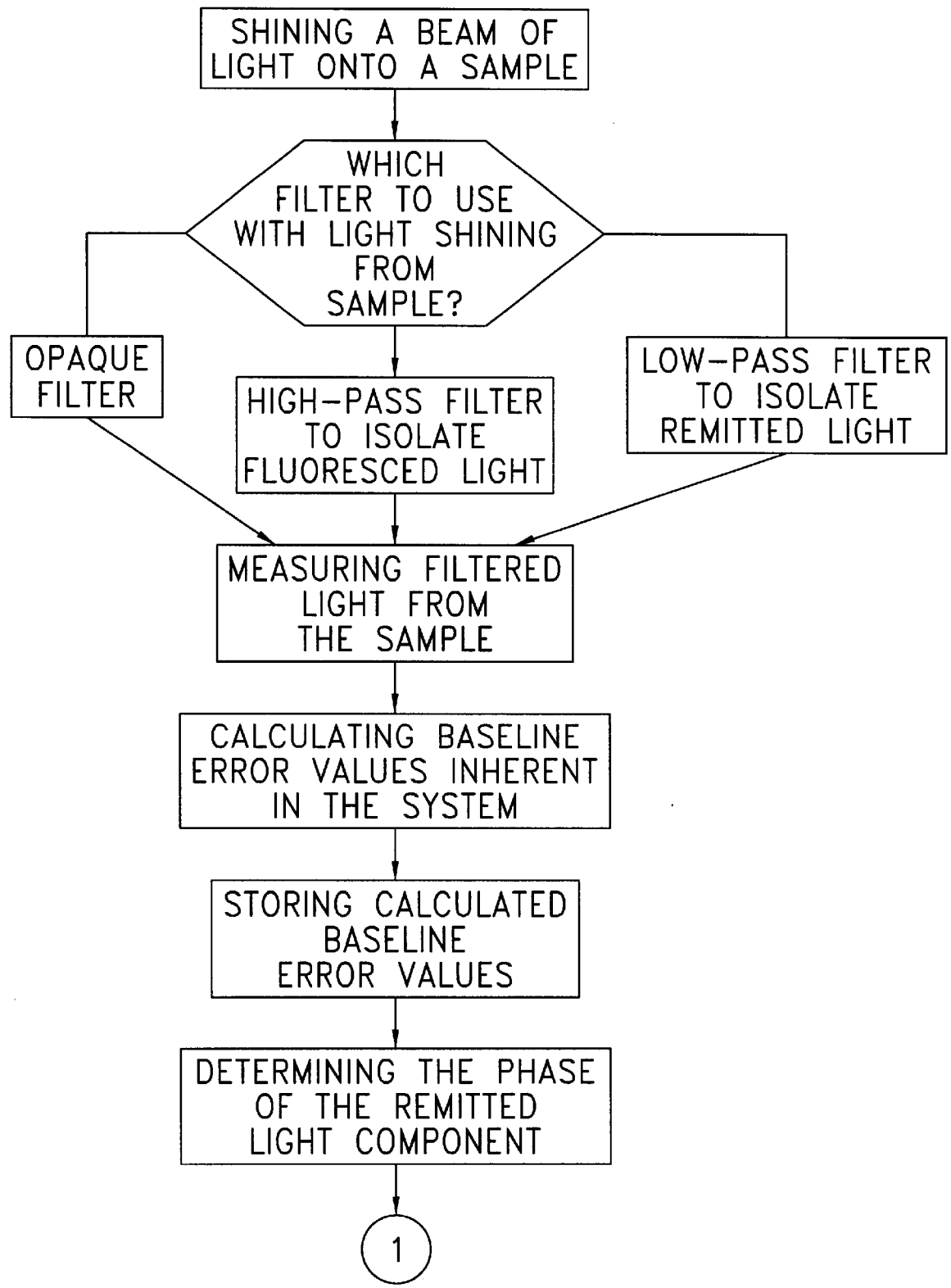
FIGS. 4 and 5 are a flow chart illustrating the process of determining lifetime fluorescence without the use of a lifetime standard.
Figure 5:
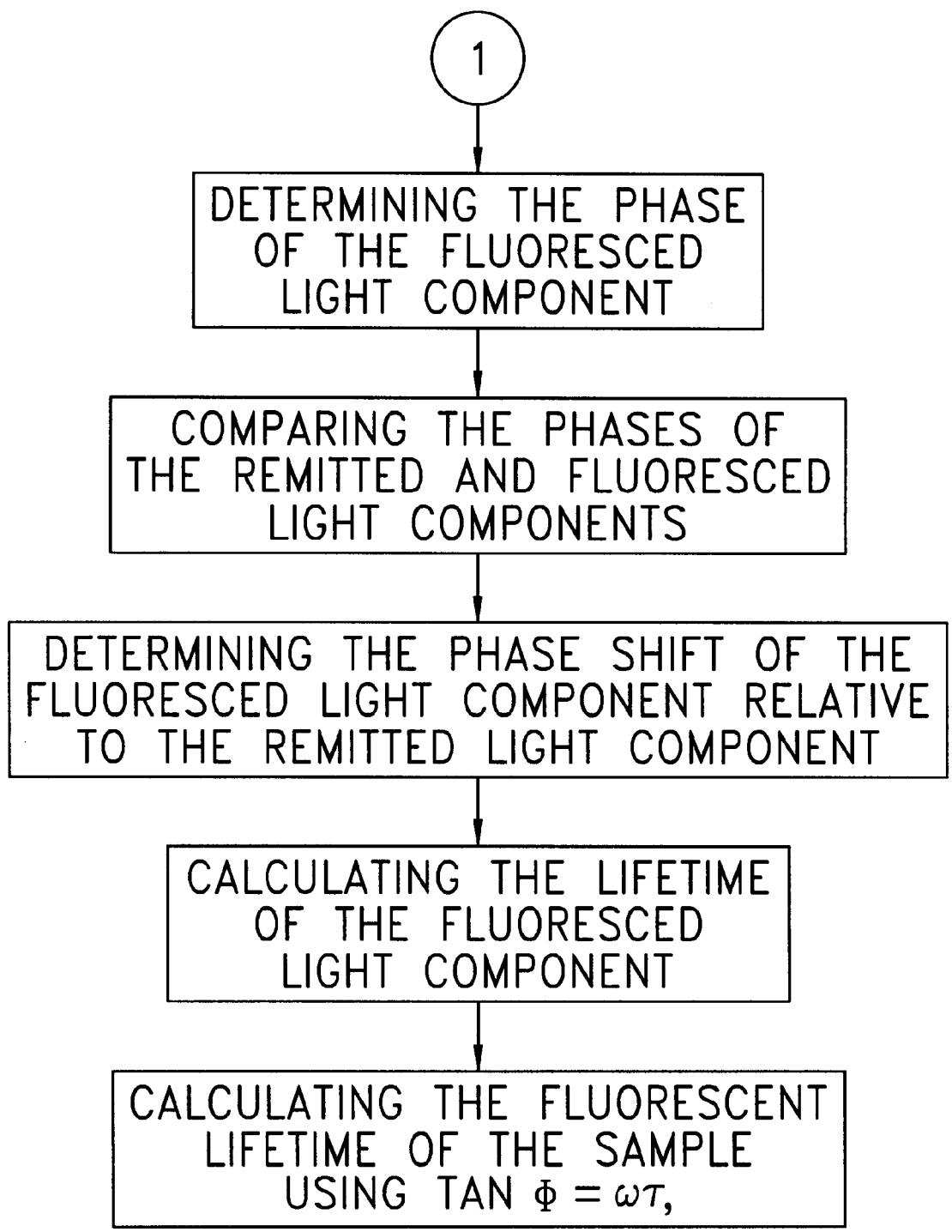

FIG. 4 charts the process of determining the fluorescent lifetime of a fluorescent unknown without the use of a reference standard. First, a filtered, energetic beam of light 14 is generated by light source 26 and shined onto a fluorescent sample 12. The light beam 14 is filtered by passing it through a low-pass source filter 24 to remove the low-frequency components that could be mistaken for a fluorescent signal. The energetic light striking sample 12 is partially reflected and partially absorbed to actuate fluorescence. Detector 30 is positioned to receive some of the remitted and fluoresced light shining from sample 12. The light shining from fluorescent sample 12 to detector 30 is selectively filtered to isolate the respective remitted and fluoresced components. Selective filtration of the light shining onto detector 30 is accomplished by selectively placing emission filters 28 between sample 12 and detector 30.

An opaque emission filter 28 is used to filter the light leaving sample 12 to generate a baseline phase and intensity value associated with fluorescent lifetime measurement apparatus 10. This value is calculated by electronic controller 32 and stored for future error correction. A low-pass emission filter 28 is placed between detector 30 and light leaving sample 12 to isolate the relatively high energy remitted light component. A high-pass filter is placed between detector 30 and light leaving sample 12 to isolate the lower energy fluoresced light component.

Detector 30 is used to respectively measure the phases of the selectively filtered light (remitted and fluoresced components) leaving fluorescent sample 12. The phase data is communicated to electronic controller 32, which subtracts the calculated baseline error contribution values inherent in fluorescent lifetime detection apparatus 10. Electronic controller 32 determines the respective phases of the remitted and fluoresced light components of the light shining from sample 12, compares the phases of the remitted and fluoresced light components, and determines the phase shift of the fluoresced light component relative to the remitted light component. Electronic controller 32 then calculates the lifetime of fluorescent sample 12 using the following equation:

$$\tan \phi = \omega \tau,$$

where $\phi$ is the measured phase shift, $\omega$ is the angular frequency of excitation of a known harmonic, and $\tau$ is the fluorescent lifetime for sample 12.

Other embodiments of the present invention have been contemplated. One such contemplated embodiment includes a filter wheel 36 having an opaque emission filter 28 and a plurality of emission filters 28 having different filter values attached thereto for example, the filter wheel might include an opaque filter and filters having values ranging from 250 to 850 nm at 50 nm intervals.

Another contemplated embodiment of the present invention includes an automatically interchangeable set of light sources 26 of different output frequencies operationally coupled to electronic controller 32, wherein the light source 26 having the output frequency best suited to stimulate fluorescence from a particular unknown desired to be measured may be selected. In other words, the functional range of the apparatus for measuring fluorescent lifetime 10 may be increased by including light sources of various output frequencies/energies so that a wider range of unknown materials may be selectively fluoresced.

Yet another contemplated embodiment combines the advantages of the above two embodiments by including both an automatically interchangeable set of light sources 26 of different output frequencies operationally coupled to electronic controller 32 and a filter wheel 36 having an opaque emission filter 28 and a plurality of emission filters 28 having different filter values attached thereto. Source beam 14 energy may be selected to best fluoresce the unknown sample 12 desired to be measured, and the relative values of the high-pass and low-pass emission filters 28 may be likewise tailored to the particular fluorescent range of the desired unknown and the excitation source beam 14.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are to be desired to be protected.

What is claimed is:

1. An apparatus for measuring fluorescent lifetime, comprising:

a light source adapted to shine a beam of light;

a low-pass source filter positioned to absorb low energy light waves from the beam of light emitted by the light source;

a sample positioned to receive the beam of light shined from the light source through the low-pass source filter;

a photodetector positioned to receive remitted and fluoresced light components from the sample;

a filter wheel adapted to selectively dispose one of a plurality of emission filters between the sample and the photodetector; and a microprocessor operationally connected to the light source; the photodetector and the filter wheel;

wherein the beam of light interacts with the sample to produce emitted sample light having a remitted component and a fluoresced component;

wherein the filter wheel includes a low-pass emission filter, a high-pass emission filter, and an opaque emission filter;

wherein the opaque emission filter is adapted to block all light remitted and fluoresced by the sample;

wherein the low-pass emission filter is adapted to selectively substantially pass the remitted component of the light from the sample and to substantially absorb the fluoresced component of the light from the sample;

wherein the high-pass emission filter is adapted to selectively substantially pass the fluoresced component of the light from the sample and to substantially absorb the remitted component of the light from the sample;

wherein the microprocessor is adapted to calculate a baseline phase from the photodetector signal received while the opaque emission filter is in place between the sample and the photodetector for subtraction from later calculations;

wherein the microprocessor is adapted to calculate a reference phase from the photodetector signal received while the low-pass emission filter is in place between the sample and the photodetector; and wherein the microprocessor is adapted to calculate the lifetime of the fluoresced signal by comparing the phase of the photodetector signal received while the high-pass filter is in place between the sample and the photodetector relative to the calculated reference phase and calculating the phase shift between the two.

2. The apparatus of claim 1, wherein a portion of the beam of light received by the sample is reflected and wherein the sample is positioned to reflect substantially the entire reflected portion of the beam of light away from the photodetector.

3. The apparatus of claim 1, wherein the source filter, the low-pass emission filter and the high-pass emission filter are selected such that the source filter and the low-pass filter substantially block the frequencies of light fluoresced by the sample while substantially passing the frequencies of light sufficiently energetic to excite fluorescence from the sample and the high-pass filter substantially passes the frequencies of light fluoresced by the sample and substantially blocks frequencies of light sufficiently energetic to excite fluorescence in the sample.

4. A lifetime fluorometer, comprising:
 a light source adapted to emit a beam of light;
 a sample holder positioned to hold a sample in the beam of light;
 a source filter positioned in the beam of light between the light source and the sample holder;
 an optical detector positioned to receive remitted and fluoresced light from the sample;
 a rotatable filter wheel having a plurality of optical filters and positioned between the optical detector and the sample; and
 a microprocessor operationally connected to the light source, the filter wheel, and the optical detector.

5. The fluorometer of claim 4, wherein the plurality of optical filters includes a low-pass filter, a high-pass filter, and an opaque filter.

6. The fluorometer of claim 4, further including a sample positioned in the sample holder and adapted to remit and fluoresce in response to the light beam.

7. The fluorometer of claim 6, wherein the sample is a biological fluid.

8. The fluorometer of claim 4, wherein the optical detector is positioned so as to receive substantially no portion of the light beam reflected from a sample in the sample holder.

9. The fluorometer of claim 5, wherein the source filter, the low-pass emission filter and the high-pass emission filter are selected such that the source filter and the low-pass filter substantially block the frequencies of light fluoresced by the sample while substantially passing the frequencies of light sufficiently energetic to excite fluorescence from the sample and the high-pass filter substantially passes the frequencies of light fluoresced by the sample and substantially blocks frequencies of light sufficiently energetic to excite fluorescence in the sample.

10. A method of determining fluorometric lifetime, comprising the steps of:
 a) shining a beam of light onto a fluorescent sample;
 b) directing a beam from the fluorescent sample containing both remitted and fluoresced light to a single detector;
 c) selectively filtering the light leaving the fluorescent sample to isolate the remitted and fluoresced components;
 d) measuring the selectively filtered light leaving the fluorescent sample; and
 e) calculating the fluorescent lifetime of the sample.

11. The method of claim 10, further comprising the steps of:
 filtering the light leaving the sample with an opaque filter;
 calculating the baseline error contribution values inherent in the system; and
 storing the baseline error contribution values for later error correction.

12. The method of claims 11, further comprising the steps of:
 filtering the light leaving the sample with a low-pass filter to isolate the remitted light component;
 measuring the remitted light component; and
 determining the phase of the remitted light component.

13. The method of claim 12, further comprising the steps of:
 filtering the light leaving the sample with a high-pass filter to isolate the fluoresced light component;
 measuring the fluoresced light component;
 determining the phase of the fluoresced light component;
 comparing the phases of the remitted and fluoresced light components;
 determining the phase shift of the fluoresced light component relative to the remitted light component; and
 calculating the lifetime of the fluoresced light component.

14. The method of claim 10, wherein the fluorescent lifetime of the sample is calculated using the following equation:

$$\tan \phi = \omega \tau,$$

where $\phi$ is the measured phase shift, $\omega$ is the angular frequency of excitation of a known harmonic, and $\tau$ is the fluorescent lifetime for the sample.

15. A method of determining the fluorescent lifetime of an unknown fluorescent sample, comprising the steps:
 a) shining light onto a fluorescent test sample;
 b) directing a beam from the fluorescent sample containing both remitted and fluoresced light to a single detector;
 c) isolating the remitted and fluoresced components of non-reflected light shining from the sample;
 d) measuring the phase characteristics of the remitted and fluorescent components of the non-reflected light shining from the sample;
 e) subtracting baseline error contributions arising from electronics associated with light generation and measurement;
 f) determining by comparison the phase shift of the fluoresced component relative the remitted component of the non-reflected light shining from the sample; and
 g) calculating the fluorescent lifetime.

16. The method of claim 15, wherein the fluorescent lifetime of the sample is calculated using the following equation:

$$\tan \phi = \omega \tau,$$

where $\phi$ is the measured phase shift, $\omega$ is the angular frequency of excitation of a known harmonic, and $\tau$ is the fluorescent lifetime for a single lifetime fluorescent indicator.

17. The method of claim 15, wherein the remitted and fluoresced components are isolated by passing the non-reflected light shining from the sample respectively through low-pass and high-pass optical filters.

18. The method of claim 15, wherein the baseline error contributions are determined by making a measurement with an opaque filter placed between the fluorescent sample and an optical detector.

19. The method of claim 15, wherein the energetic light beam shined on the sample is filtered to remove low-energy components that could be mistaken for light fluoresced from the sample.

20. The method of claim 15, wherein the energetic light beam shined on the sample is filtered to remove low-energy components that could be mistaken for light fluoresced from the sample;
   wherein the baseline phase and offset contributions are determined by making a measurement with an opaque filter placed between the fluorescent sample and an optical detector;
   wherein the remitted and fluoresced components are isolated by passing the non-reflected light shining from the sample respectively through low-pass and high-pass optical filters; and
   wherein the fluorescent lifetime of the sample is calculated using the following equation:

$$\tan \phi = \omega \tau,$$

where $\phi$ is the measured phase shift, $\omega$ is the angular frequency of excitation of a known harmonic, and $\tau$ is the fluorescent lifetime for the sample.

* * * * *